United States Patent [19]

Cavicchi et al.

[11] Patent Number: 5,356,756
[45] Date of Patent: Oct. 18, 1994

[54] APPLICATION OF MICROSUBSTRATES FOR MATERIALS PROCESSING

[75] Inventors: Richard Cavicchi, Washington Grove; Stephen Semancik, Mt. Airy; John S. Suehle, Westminster; Michael Gaitan, Gaithersburg, all of Md.

[73] Assignee: The United States of America as represented by the Secretary of Commerce, Washington, D.C.

[21] Appl. No.: 965,943

[22] Filed: Oct. 26, 1992

[51] Int. Cl.$^5$ .............................................. C23C 16/00
[52] U.S. Cl. ......................................... 430/315; 427/8; 427/10; 427/96; 427/126.3; 427/255; 427/282; 427/376.2; 204/192.12
[58] Field of Search ................ 427/96, 126.3, 10, 255, 427/282, 376.2, 8; 204/192.12; 430/315

[56] References Cited

U.S. PATENT DOCUMENTS

| | | | |
|---|---|---|---|
| 3,509,431 | 4/1970 | Iles et al. | 257/443 |
| 3,571,917 | 3/1971 | Merryman et al. | 29/573 |
| 4,103,073 | 7/1978 | McAlear et al. | 428/474 |
| 4,142,925 | 3/1979 | King et al. | 148/175 |
| 4,181,544 | 1/1980 | Cho | 148/175 |
| 4,286,377 | 9/1981 | Hurko et al. | 29/612 |
| 4,292,730 | 10/1981 | Ports | 29/577 |
| 4,293,624 | 10/1981 | Buckley | 427/96 |
| 4,425,379 | 1/1984 | Vora et al. | 437/175 |
| 4,470,875 | 9/1984 | Poteat | 156/644 |
| 4,574,264 | 3/1986 | Takahashi et al. | 338/34 |
| 4,612,083 | 9/1986 | Yasumoto et al. | 156/633 |
| 4,706,061 | 11/1987 | Honeywell, Inc. | 338/34 |
| 4,728,591 | 3/1988 | Clark et al. | 430/5 |
| 4,743,954 | 5/1988 | Brown | 257/253 |
| 4,824,803 | 4/1989 | Us et al. | 437/192 |
| 4,897,361 | 1/1990 | Harriott et al. | 437/24 |
| 4,897,814 | 1/1990 | Clark | 365/49 |
| 4,918,032 | 4/1990 | Jain et al. | 437/228 |
| 4,985,373 | 1/1991 | Levinstein et al. | 437/195 |
| 5,019,885 | 5/1991 | Yagawara et al. | 73/23.4 |
| 5,050,091 | 9/1991 | Rubin | 364/488 |
| 5,071,770 | 12/1991 | Kolesar, Jr. | 436/151 |
| 5,075,250 | 12/1991 | Hawkins et al. | 437/52 |
| 5,131,954 | 7/1992 | Vogeli et al. | 136/244 |

FOREIGN PATENT DOCUMENTS 0285833 10/1988 European Pat. Off. .
1218211 1/1971 United Kingdom .................. 427/96

OTHER PUBLICATIONS

"A Planar Integrated Chlorinated Hydrocarbon Gas Sensor on a Silicon Substrate", D. Keyvani et al; Sensors and Actuators, B. 5 (1991) pp. 199–203.

(List continued on next page.)

Primary Examiner—Shrive Beck
Assistant Examiner—Vi Duong Dang
Attorney, Agent, or Firm—Michael S. Gzybowski

[57] ABSTRACT

Arrays of microfabricated hotplates have been used as substrate arrays for materials processing on a microscopic scale. Properties of individual elements (pixels) of the array, such as temperature and voltage bias, are controlled by addressing a given pixel with appropriate signals. Materials are deposited onto pixels with individually controlled deposition conditions (pixel temperature, bias). Pixels are also addressed to control properties during post-deposition processing steps such as heating in vacuum or various gases to alter stoichiometry of a single material, or to alloy multiple composition materials. The addressable heating characteristics may also be used for a maskless lithography on pixel elements. The result is an array of separately, but simultaneously, processed films. Properties of film elements may be measured using electrical contact pads. The array of processed films may be used for sensors, electronic devices, greatly accelerated materials development processes, and solid state physics, biology and chemistry studies.

20 Claims, 9 Drawing Sheets

OTHER PUBLICATIONS

"The Si Planar Piellistor: A Low-Power Pellistor Sensor in Si Thin-Film Technology", M. Gall; Sensors and Actuators, B. 4 (1991) pp. 533–538.

"Handbook of Thin Film Deposition Processes and Techniques: Principles, Methods, Equipment, and Applications", edited by K. Schuegraf. Noyes Publications, Park Ridge, N.J. 1988.

N. Najafi, K. D. Wise, R. Merchant, and J. W. Schwank, "An Integrated Multi-Element Ultra-Thin-Film Gas Analyzer" *IEEE Workshop on Sensors*, Hilton Head, S.C. (1992), p. 19.

Jaeggi et al, "A CMOS Process for Micromachining a Thermoelectric AC Power Sensor", *IEEE Trans. On Electron Devices*, vol. 13, No. 7, p. 366 (1992).

M. Parameswaran et al, "Micromachined Thermal Radiation Emitter from a Commercial CMOS Process," *IEEE Electron Device Letters*, vol. 12, No. 2 (1991) pp. 57–60.

APPLICATION OF MICROSUBSTRATES FOR MATERIALS PROCESSING

TECHNICAL FIELD

The present invention relates to materials processing methods. More particularly, the present invention relates to the adaptation of microsubstrates having arrays of individually controllable micro-hotplates to materials processing techniques.

BACKGROUND ART

Development of thin film materials conventionally involves subjecting macroscopic (>1 cm) samples to a sequence of deposition, lithographic and post-deposition processing steps. Microlithography technology has been used to isolate microscopic regions for deposition or etching of materials to produce different devices on a single wafer. However, during a given process the entire sample or wafer is held at given temperature. Wafer processing sequences are constrained by "thermal budgets" in which processing steps for the wafer are limited by the lowest maximum temperature tolerance of any other device or layer on the wafer.

From another point of view, scientific studies to optimize a process sequence for a thin film (for coating or device applications, for example), usually involve successive runs through a cycle using varying process temperatures for each run. Since process steps involve mounting the sample in a chamber for controlled environments (high vacuum, furnace, plasma etching, etc.) a full cycle for one sample may require a day or longer to process.

Using micro-machining techniques, it has become possible to create small (<0.1 mm) structures on silicon wafers that are thermally isolated from the rest of the wafer. These structures may be equipped with microlithographically-defined heater elements to reach temperatures in excess of 1000° C., while the rest of the wafer is at ambient room temperature. A recent example is the integrated multi-element gas analyzer by Najafi et al (N. Najafi, K. D. Wise, R. Merchant, and J. W. Schwank, IEEE Workshop on Sensors, Hilton Head, S.C., 1992), pp. 19). This work uses micromachining techniques to fabricate an integrated heater, metal dispersant layer, silicon temperature sensor, and gas-sensing film. The heating element is used to thermally activate sensing adsorption/desorption phenomena occurring on the gas-sensing film surface. Use of the heater to process materials was not considered. The technique used to fabricate the structure was a special process that does not take advantage of low-cost commercial foundry capabilities.

DISCLOSURE OF THE INVENTION

It is accordingly one object of the present invention to provide a method of characterizing materials.

Another object of the present invention is to provide a method of investigating micro-samples (<1 cm) of materials.

A further object of the present invention is to provide a method of preparing a plurality of micro-samples.

It is a further object of the present invention to provide a method of preparing a plurality of micro-samples on a single substrate which have different characteristics.

A still further object of the present invention is to provide a method of preparing a plurality of micro-samples for investigation.

A still further object of the present invention to provide a method of maskless lithography.

According to these and further objects of the present invention which will become apparent as the description thereof proceeds, there is provided a method of preparing a plurality of micro-samples of materials for investigation which involves:

providing a substrate having a plurality of micro-hotplates, wherein each of the plurality of micro-hotplates can be individually temperature controlled; and depositing a material film on the plurality of micro-hotplates while thermally cycling selected ones of the plurality of micro-hotplates to form a micro-sample on each of the plurality of micro-hotplates.

The present invention further provides a method of characterizing material properties which involves:

providing a substrate having a plurality of micro-hotplates, wherein each of the plurality of micro-hotplates can be individually temperature controlled;

depositing a material film on the plurality of micro-hotplates while thermally cycling selected ones of the plurality of micro-hotplates to form a micro-sample on each of the plurality of micro-hotplates; and characterizing properties of the micro-samples.

BRIEF DESCRIPTION OF DRAWINGS

The present invention will hereafter be described with reference to the annexed drawings which are given by way of non-limiting examples only in which.

BEST MODE FOR CARRYING OUT THE INVENTION

Figure 1A:
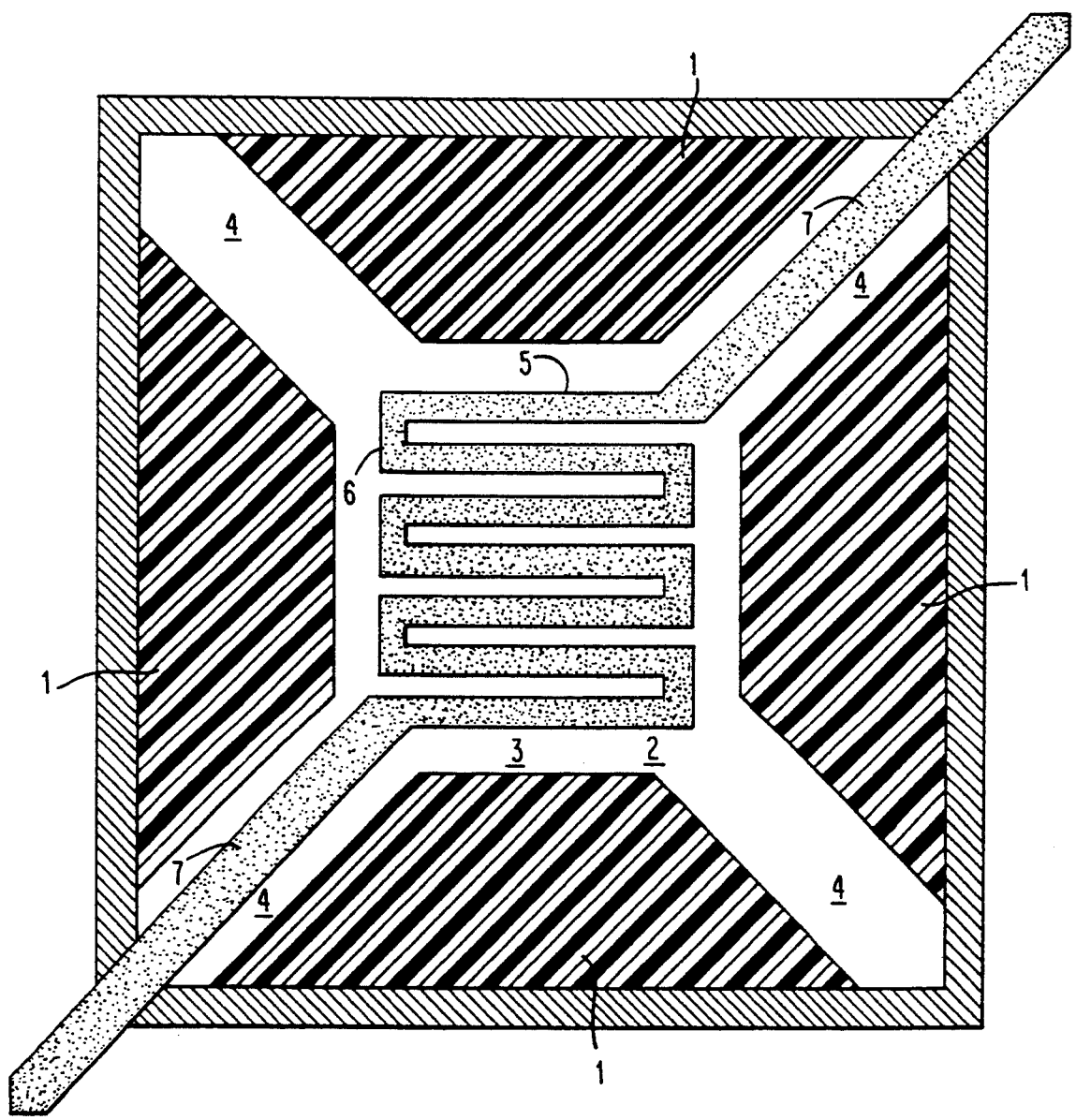
FIG. 1A is a schematic drawing showing the open areas and the heating element according to one embodiment of the present invention.

A commercial CMOS process has recently been developed at the National Institute of Standards and Technology (NIST) to form micro-heater structures using commercial foundries designed to produce application specific integrated circuits (ASIC). This technology allows lamp drivers and multiplexers to be mounted on a single chip as the microlamps using existing technology. These structures were designed to produce microlamp arrays, to be used for infrared-visible displays. A CMOS process for micromachining a thermoelectric AC power sensor was also recently described by Jaegi et al (D. Jaegi, H. Baltes, and D. Moser, IEEE Trans. on Electron Devices 13, 366 (1992)).

The inventors of the present invention have refined the structure of the NIST device to include a temperature-dispersant, temperature-measuring hotplate, and a set of four contacts to a top layer film. This refined structure is related to the structure of Najafi et al, with two significant differences: First, the procedure developed by the present inventors uses MOSIS foundry technology, making the device of lower cost, enabling devices to be fabricated with much less expensive capital equipment, and allowing simple on-chip fabrication of other electrical components such as drivers and multiplexers, which, in turn, greatly reduces wiring problems associated with large arrays. Second, the structure developed by the present inventors uses a four-point temperature measurement, which is more accurate than two-point resistance measurements.

In developing this new micro-hotplate, the present inventors recognized that such microstructures could be used to individually and addressably process materials grown on them. Accordingly, the present invention was developed for applications of the microstructures, including micro-hotplates, for materials processing.

Previous work has only considered processing materials in a batch mode, in which the entire wafer or macroscopic (>1 cm) substrate is subject to a fixed set of process parameters. A reference for this type of procedure is the "Handbook of Thin Film Deposition Processes and Techniques: Principles, Methods, Equipment, and Applications", edited by K. Schuegraf (Handbook of thin film deposition processes and techniques: principles, methods, equipment, and applications (Noyes Publications, Park Ridge, N.J., 1988)).

The present invention is directed to applications of micro-hotplate or micro-substrate structures for micro-materials processing. The present invention uses depositions of materials and subsequent processing on an array of individually temperature controlled micro-hotplates to perform parallel exploration of a wide parameter space for materials processing. According to the present invention, as many as 1000 micro-samples can be formed in the time required to process one sample by conventional techniques. Sample characterization by scanning electron microscopy, and other microcharacterization techniques can similarly be accelerated utilizing the methods of the present invention as discussed below.

The technology of the present invention circumvents the thermal budget problem described above, since each micro-hotplate is thermally isolated from the others on the chip. The small structure of the micro-hotplates or microstructures used according to the present invention allow particular advantages in the field of materials processing such as rapid quenching, and rapid temperature change which can produce new materials; and maskless lithography, which provide uses for the micro-hotplates or microstructures The present invention involves the use of micro-hotplate devices each of which includes a heating element that is thermally isolated on a suspended membrane or microbridge and a conductive heat distribution plate which is above and electrically isolated from the heating element. The conductive heat distribution plate includes electrical leads which allow for temperature sensing and control.

A plurality of conductive pads, e.g. four, are provided above the conductive heat distribution plate, and are electrically isolated therefrom by an intermediate layer of insulation material. Another electrical insulation layer is provided over the conductive pads, with openings therein which allow each of the conductive pads to be exposed to the external or ambient environment. The conductive pads are used to sense properties of materials which come into contact therewith.

The micro-hotplates used in the present invention can be fabricated using standard CMOS compatible micromachining processes. To form the suspended membrane of microbridge structure, a wafer or chip of silicon which includes a top layer of an insulation material such as silicon dioxide is provided with openings in the top layer of insulating material so as to expose portions of the underlying silicon surface. These openings can be designed and implemented without any additional masking at any CMOS foundry. If the openings are properly laid-out according to the present invention, a suspended membrane or microbridge with support legs will be formed in a post-fabrication etch process described below.

Standard CAD software used to design devices and circuits to be manufactured in integrated circuit processes can be used to design the micro-hotplate(s) used in the present invention. Therefore, large numbers of the micro-hotplates can be designed and fabricated on a single support substrate, i.e. wafer or chip, using conventional CMOS techniques.

There are a number of available software packages available which can be employed according to design the micro-hotplates. One such software package which is available from the public domain and has been employed by the inventors during the course of the present invention is called MAGIC.

In order to use software packages such as MAGIC to design openings for the micromachining step, the technology file used in the software has to be modified. According to the modification, which is known and reported elsewhere (J. Marshall, M. Parameswaran, M. Zaghloul and M. Gaitan, "Methodology for the Computer-Aided Design of Silicon Micromachined Devices in a Standard CMOS Process", NISTIR, May 1992), a new layer, which in the present invention is referred to as "open" is formed. This layer is composed of IC fabrication masks that are available in standard CMOS processes but which are not normally used together, namely the glass cut, metal contacts, and poly and active area contacts. It is noted that while reference herein is made to the use of MAGIC, other CAD software packages could also be similarly modified in order to design the openings used in the micro-hotplates.

FIG. 1A shows the design of the openings and the heating element used according to one embodiment of the micro-hotplates. As shown in FIG. 1A, four openings 1 are provided along each side of the device. The openings 1 expose the underlying silicon substrate, leaving a membrane or microbridge structure 2 which, after fabrication of the device is caused to be suspended by a post-fabrication etch process. The post-fabrication etch process forms an etch pit 18 (FIG. 4) beneath the membrane or microbridge 2. In a preferred embodiment, the membrane or microbridge 2 is formed of an insulation material such as glass, e.g. silica, which provides mechanical support for the suspended structure and electrical insulation. The final suspended nature of the membrane or microbridge 2 itself provides thermal insulation of the device.

For some applications (for example, epitaxy of an overlayer) it may be desired to have single crystal Si available on a suspended surface. This can be achieved by either etching a Si wafer from the backside, or through the use of implanted oxidation of silicon (SIMOX) techniques and doping etch stops. For other applications, very small structures may be desirable. Electron beam lithographic techniques may be useful for obtaining small size.

In FIG. 1A, the membrane or microbridge 2 is depicted as having a square central portion 3 and four support legs 4 which extend from corners of the central portion 3 to the edge of the device. The choice of design layouts for the openings 1 and resulting membrane or microbridge 2 is not limited to that shown in FIG. 1A. Other design layouts could also be used as long as they result in a suspended membrane or microbridge 2. For example, more or less than four support legs could be used to support a central membrane or microbridge portion. In this regard, a cantilevered structure could be used a well as a rectangular membrane which is supported at opposite ends to the edge of the device.

The heating element 5 shown in FIG. 1A includes a serpentine ribbon portion 6 of a conductive material which has leads 7 at opposite ends thereof. The leads 7 extend over the support legs 4 as shown. The heating element 5 functions as a resistive heater when an electrical current is applied to the leads 7 thereof. The heating element 5 can be made of any conductive material including metals or metalloids or compounds thereof. However, a polysilicon heating element was found to be particularly suitable for purposes of the present invention.

In addition to functioning as a source of heat, the heating element 5 can also be used to sense temperature in a known manner. Thus, according to one embodiment of the present invention, the heating element 5 can be used as a resistive heater and as a temperature sensor. Accordingly to another embodiment of the invention, two separate parallel conductive lines are provided; one serving as a heater and the other serving as a temperature sensor.

Figure 1B:
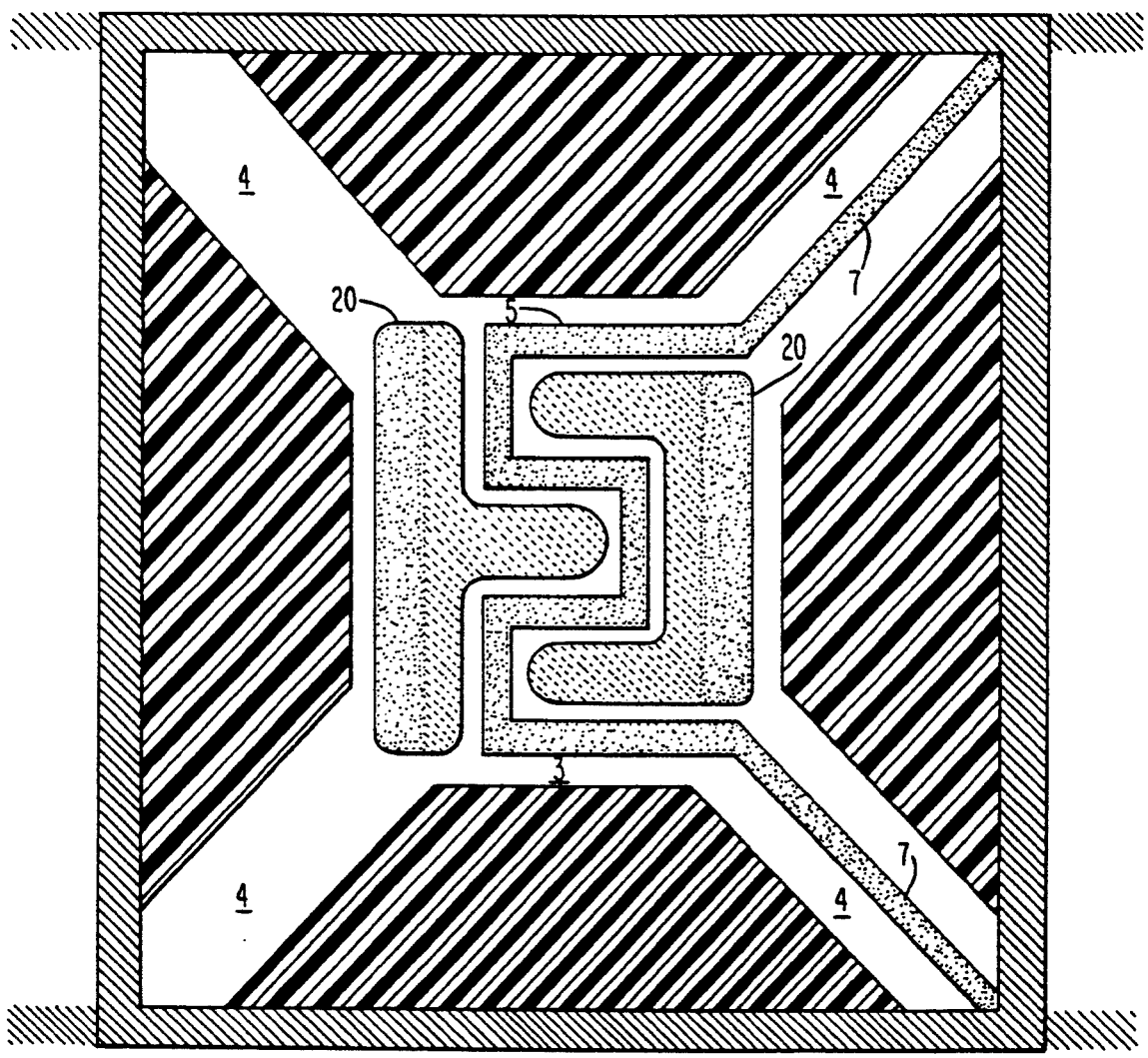
FIG. 1B is a schematic drawing showing an alternative embodiment of the heating element.

FIG. 1B is a schematic drawing showing an alternative embodiment of the heating element which includes adjacent, co-planar heat distribution elements or "islands". As depicted in FIG. 1B, the heating element 5 does not extend across the whole surface area of the central portion 3 of the membrane or microbridge 2. The surface area of the central portion 3 of the membrane or microbridge 2 which is not covered by the heating element 5 is provided with islands 20 of heat conducting material which are co-planar with the heating element 5. The material from which the heat conducting islands 20 are made can be the same or different from the material from which the heating element 5 is made. For example, both the heating element 5 and the heat conducting islands 20 can be made from polysilicon, which is thermally more conducting than silicon dioxide. The heat conducting islands 20 need not be connected to electrical leads. The heat conducting islands 20 can also be used in conjunction with the co-planar temperature sensor discussed above.

For convenience, all the materials used in the microstructure device should be selected from those available from, or compatible with, standard CMOS processes. Commercial CMOS processes can be employed which can provide layers of polysilicon and aluminum; these processes can be used in known manners to fabricate the contacts, heaters, and temperature sensors used in the devices of the present invention.

Figure 2:
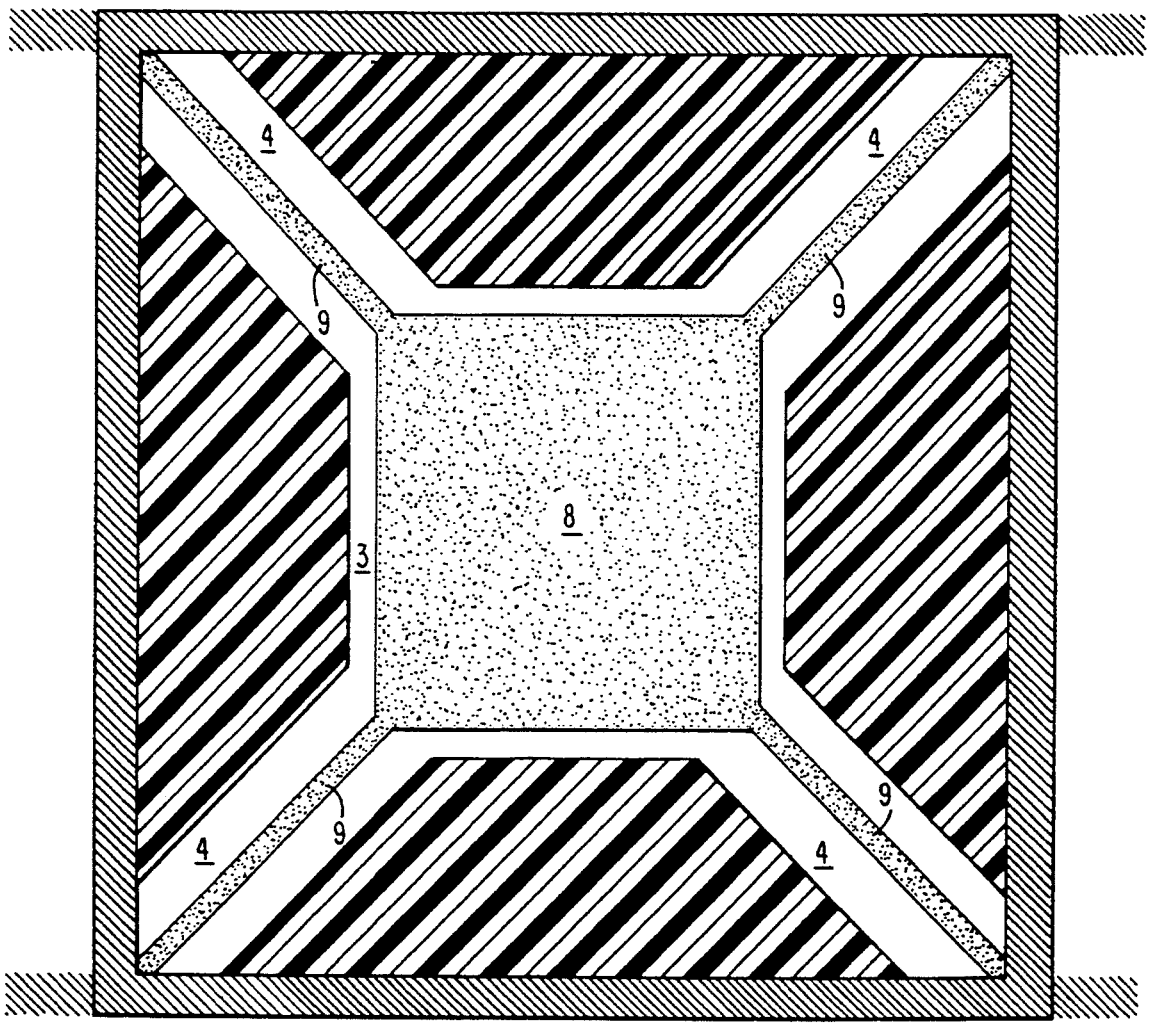
FIG. 2 is a schematic drawing showing the conductive heat distribution plate with four point contacts according to one embodiment of the present invention.

FIG. 2 shows the conductive heat distribution plate used in the micro-hotplate according to one embodiment of the present invention. The conductive heat distribution plate 8 is provided on top of the central portion 3 of the membrane or microbridge 2 and has a surface area which is preferable coextensive and aligned with the central portion 3 of the membrane or microbridge 2, or at least coextensive and aligned with the heating element 5, absent the leads thereof. The conductive heat distribution plate 8 and membrane or microbridge 2 are separated by a layer of insulating material 13 (FIG. 4) such as glass, e.g., silica, which provides electrical insulation therebetween. One of four leads 9 extend from each corner of the conductive heat distribution plate 8 on the support legs 4 as shown. These leads 9 allow for temperature sensing by measuring resistivity of the metallic heat distribution plate 8. In this regard, two of the leads are used for voltage sensing and the other two leads are used as current source lines in a conventional manner.

The conductive heat distribution plate 8 functions both to evenly distribute heat from the heating element 5 to the top surface of the micro-hotplate and as a means to sense temperature near the top surface. In this regard, the temperature is sensed by measuring the change in resistivity of the material from which the conductive heat distribution plate 8 is made as a function of temperature. This resistivity change is characterized by a term called the temperature coefficient of resistance, (TCR) and can be determined by measurements using an external hot plate as a reference in a conventional manner. The conductive heat distribution plate 8 can be made from any metal or metalloid or compounds thereof which conducts heat and can withstand temperatures at which the device is to be used. For purposes of the present invention aluminum was found to be suitable material from which to make the conductive heat distribution plate 8. However, the conductive heat distribution plate 8 could be made from conductive materials having higher melting temperatures if the device is to be operated at high temperatures.

Figure 3:
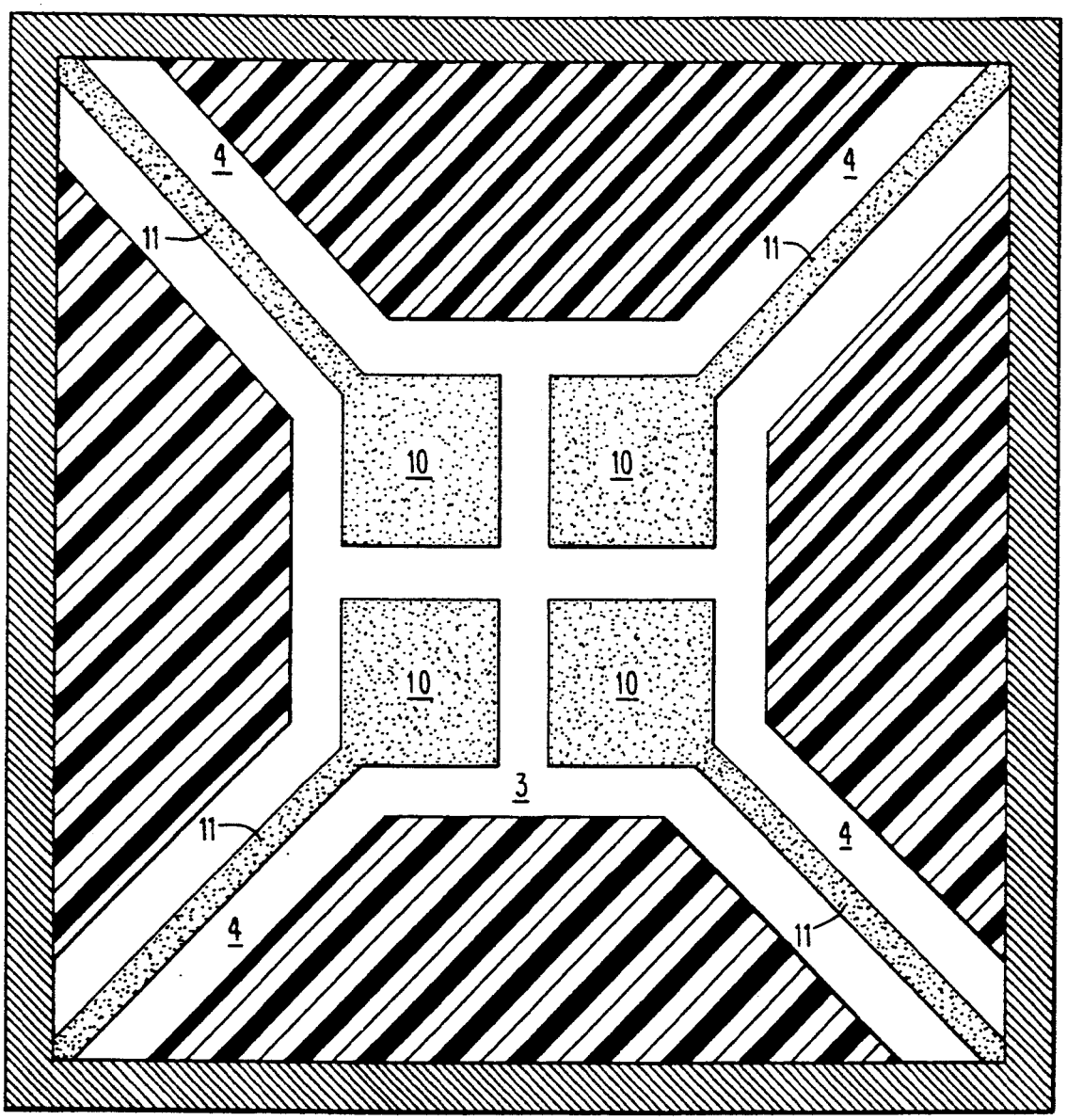
FIG. 3 is a schematic drawing of the second level of metal contacts according to one embodiment of the present invention.

FIG. 3 shows the contact pads that are exposed to the external or ambient environment to which the device is exposed. As shown in FIG. 3 the contact pads 10 are symmetrically arranged over the conductive heat distribution plate 8. An electrical insulating layer 14 (FIG. 4) such as a glass, e.g., silica, is provided between the contact pads 10 and the conductive heat distribution plate 8. The contact pads 10 are covered by another layer 15 (FIG. 4) of an electrical insulating material such as glass, e.g., silica, which includes a like number of openings 16 (FIG. 4) that allow each of the contact pads 10 to be exposed to the external or ambient environment.

In operation, as discussed below, the contact pads 10, which are made form a conductive material such as metals or metalloids or compounds thereof, are used as point contacts to measure the resistance of materials, i.e., solids, liquids or gas which come into contact with, or are formed on, the contact pads 10 on the top of the device. For this purpose, conductive leads 11 extend from each of the contact pads 10 on the support legs 4 as shown.

Figure 4:
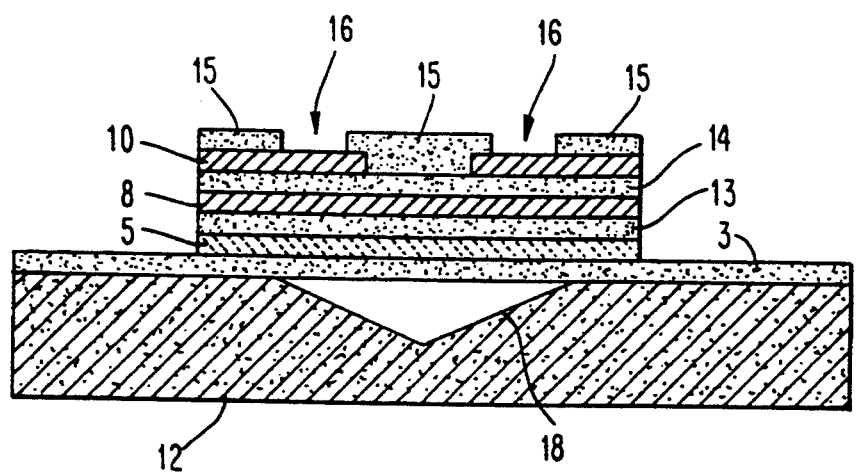
FIG. 4 is a schematic cross-sectional view of the micro-hotplate according to one embodiment of the present invention.

FIG. 4 is a schematic cross-sectional view of the micro-hotplate according to one embodiment of the present invention. As depicted in FIG. 4, according to a preferred embodiment, each micro-hotplate device has a suspended membrane or microbridge together with layers of polycrystalline silicon (PXS), silicon dioxide ($SiO_2$), and aluminum (Al). These preferred materials are compatible with the CMOS processes used to fabricate the devices on the chip. The layer sequence on the silicon chip from bottom to top as shown includes the suspended membrane or microbridge 2 which is made of silicon dioxide, the heating element 5 which is made of polycrystalline silicon, an insulating layer 13 of silicon dioxide, the conductive heat distribution plate 8 which is made of aluminum, another insulating layer 14 of silicon dioxide, four contact pads 10 which are made of aluminum, and a final insulating layer 15 of silicon dioxide with four openings 16 therein which communicate with the contact pads in the layer below.

Figure 5:
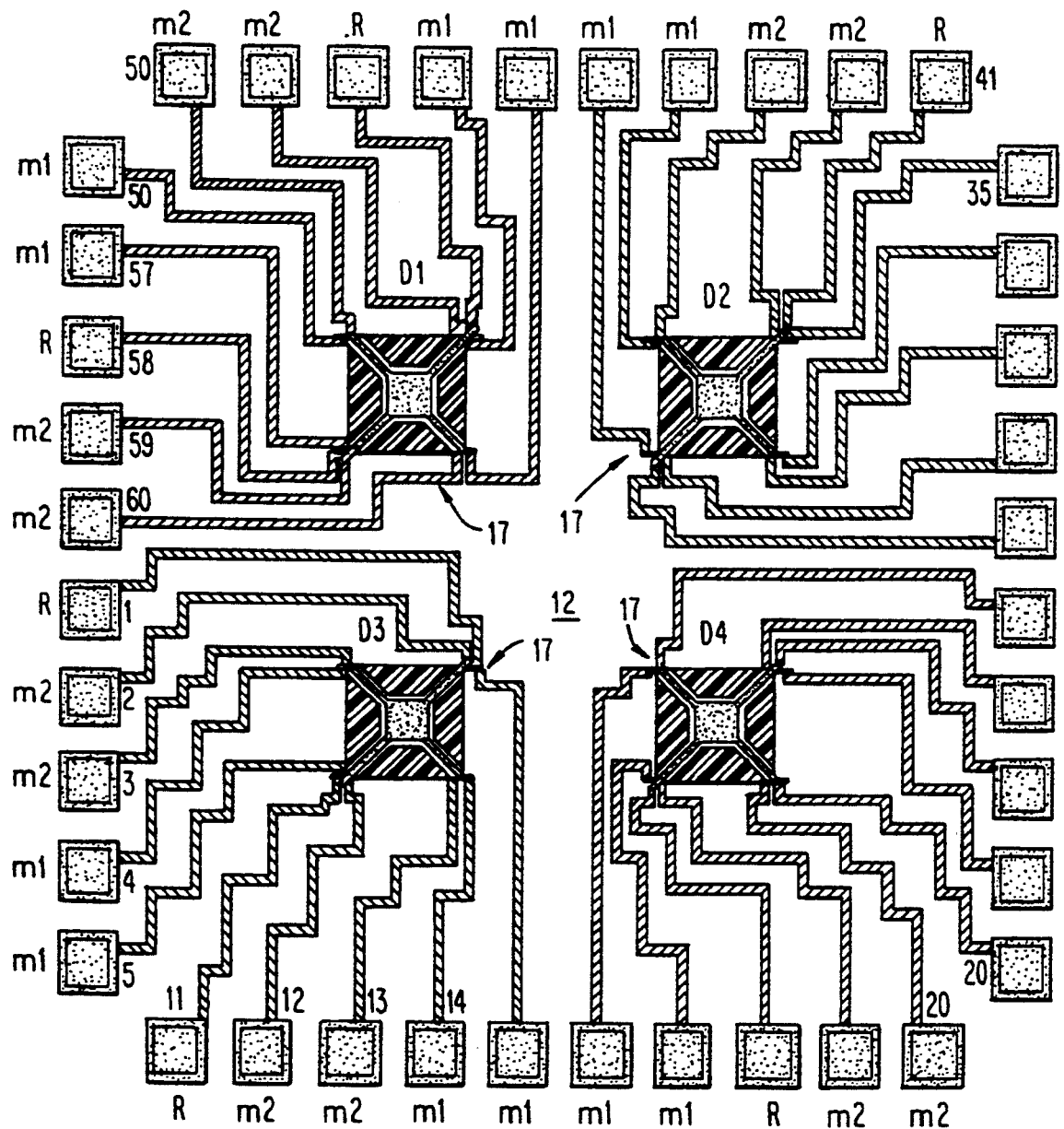
FIG. 5 is a schematic drawing of an array of four micro-hot plates on a single substrate according to the present invention.

FIG. 5 shows an array of four micro-hot plates on a single substrate according to the present invention. As shown in FIG. 5, the array includes a substrate support 12, e.g., a silicon chip, with an array of four micro-hotplates 17 with 10 leads per device. It is noted that while four micro-hotplates are shown in the array of FIG. 5, it is a simple matter to use the same technology to produce hundreds of similar devices on a single support substrate, i.e., a wafer or chip.

In operation, a suitable current of up to about 100 mA, and more typically about 4 mA to 20 mA is applied to the leads 7 of the heat element 5. In response, the device heats up to a temperature related to the current. Temperature is measured by supplying a suitable current of up to about 50 mA, and more typically 10 mA, to two of the four leads 9 of the conductive heat distribution plate 8 and measuring the voltage drop, which is generally up to about 10 mV, and more typically about 1 mV, across the other two leads of the conductive heat distribution plate 8.

The device depicted in FIG. 4 and discussed above, has an operable temperature range of from ambient temperature (normally room temperature, although the chip may be mounted on a cold surface to obtain lower temperatures) to about 600° C. Above 600° C., aluminum begins to deform (by electromigration, etc.) and eventually melt. The device can be easily designed to operate at higher temperatures, e.g., up to 1200° C. by replacing the aluminum elements with polysilicon. For materials science studies at high temperatures in oxidizing environments, one may use a top layer of Pt to serve as a platinum resistance thermometer. Thin film thermocouple elements may also be included to measure temperature in some applications.

Foundry processes that use metals other than aluminum, e.g., tungsten, will allow other metals to be used in the devices of the present invention and will provide micro-hotplates than can operate at much higher temperatures.

For clarity, the wire connections to each of the leads of the micro-hotplates has not been shown. However, in use, the chip supporting one or more micro-hotplates is mounted on a ceramic chip carrier, having conventional connections between the chip and carrier leads accomplished using gold wirebonds.

The size of the initial micro-hotplate that was designed was 200 micrometers on a side. However this initial size is certainly not limiting since it is clear that other sizes could be chosen. In this regard, the present inventors have successfully designed and fabricated similar layouts to produce devices in a range of 50 micrometers to 800 micrometers.

No limitations have yet been encountered which limit the large end size at which a device can be made. However, small devices less than 50 micrometers may not be desirable since good thermal isolation may not be achieved.

Once the device is designed using CAD software, the file can be saved for future use. Since the devices used in the present invention are manufactured using standard CMOS processes, conventional circuits can be added for temperature control and sensing and communication according to known techniques. It is noted that other silicon foundry processes are available such as BICMOS, BIPOLAR, etc. and that this methodology is also compatible with those processes.

While the device used in the present invention is designed by making use of standard CMOS compatible micromachine processes, CMOS foundries do not currently offer the additional post-fabrication etching step required to form the suspended membrane or microbridge structure of the present invention. Therefore, this step is carried out after the CMOS fabrication process. This method of providing suspended membranes or microbridges has been shown to provide good thermal isolation in other devices (M. Parameswaran et al, "Micromachined Thermal Radiation Emitter from a Commercial CMOS Process", *IEEE Electron Device Letters*, Vol. 12, No. 2 (1991), pages 57–60).

After the designs are fabricated, the completed chips are subjected to a post-fabrication etch procedure to complete the fabrication of the device. In the post-fabrication etch a mixture of ethylenediamine-pyrocatechol-water-pyrazin (EDP, Transene Company) is utilized to form an etch pit 18 (FIG. 4) beneath at least the central portion 3 of the membrane or microbridge 2. EDP can be mixed in-house as reported in the literature (Jaeggi et al, "Thermoelectric AC Power Sensor by CMOS Technology", *IEEE Electron Device Letters*, Vol. 13, No. 7 (1992), page 366).

In the post-fabrication etch procedure aluminum hydroxide $Al(OH)_3$ is preferably added to the EDP in order to limit the attack of the EDP on exposed aluminum surfaces. The mixture was heated in a reflux container to 97° C. and the devices were etched for approximately 1 hour 15 minutes. After this step the fabrication is complete and the devices can be packaged and tested.

According to one embodiment, electroplating and electroless plating have been utilized to deposit barrier materials such as nickel and copper on exposed aluminum contact pads and on exposed silicon regions in order to protect these layers from the echant and to increase the operable temperature range of the device. This plating can be performed selectively on the contact pads, or the exposed silicon regions, or both utilizing maskless deposition techniques.

Thermal isolation is necessary in order to heat the surface to elevated temperatures (in the range of ambient to about 1200° C.) at power levels that are compatible with IC-based applications (less than 100 mW per heater).

Thermal response time and power requirements of the device may be controlled by limiting or increasing the number and size of the legs 4 and the various electrical leads on the legs. In general, higher thermal conducting paths (more and/or shorter legs and more and- /or larger electrical leads) will provide a faster response time (on the order of one microsecond or less) at a higher power requirement. Fewer legs and less electrical leads will provide a lower power requirement, but a slower response time.

Devices have been fabricated which have a response time of about 1 millisecond and require 10 mW of power to attain a temperature of 500° C.

It is to be understood that the present invention is directed to applications which utilize the above-described micro-hotplates which the present inventors have developed. However, while it is preferred to utilized the above-described micro-hotplates because their unique temperature distribution and monitoring ability, other structures which provide individually controlled pixel heating elements could also be used for materials processing according to the present invention.

As discussed above the present invention is directed to applications of micro-hotplate or micro-substrate structures for micro-materials processing. In this regard, the present invention uses depositions of materials and subsequent processing on an array of individually temperature controlled micro-hotplates to perform parallel exploration of a wide parameter space for materials processing.

To perform deposition, a deposition system was used which was outfitted with vacuum compatible socket into which the microsubstrate was inserted. The socket was composed of high temperature low-outgassing plastic; however, ceramic sockets are available which are compatible with even better vacuums.

Connections to instruments external to the deposition system were accomplished using vacuum feedthroughs. These instruments included current sources to drive the heating element, the conductive heat distribution plate, and the contact pads, and instruments to measure the voltage difference between two points on the conductive heat distribution plate and between two of the contact pads.

The microsubstrate package was mounted in its socket in the vacuum system. The socket was mounted on a rotary-linear drive which allowed the sample to be positioned in the vacuum system to face various deposition sources and processing equipment. Prior to deposition, the individual microsubstrates were annealed in vacuum (by supplying current to the microheaters and measuring temperature using the conductive heat distribution plates) to desorb any contaminants. If desired, the surface may be further cleaned by argon ion sputtering, e.g., using a commercial 2 kilovolt source at a pressure of $10^{-3}$ Pa. If argon ion sputtering is used to clean the surfaces of the microsubstrates, care must be taken to avoid buildup of electrostatic charge during ion sputtering, for example by grounding components.

Many deposition techniques, and materials, including conductive and semiconductive materials, formed thereby, can be studied according to the present invention, including DC and RF sputtering, thermal and electron beam evaporation, chemical vapor deposition, and the like.

According to an exemplary deposition procedure, films of $SnO_2$ were prepared by reactive RF sputtering. This technique uses a chamber pumped to high vacuum, e.g., from less than $10^{-4}$ Pa and typical $10^{-6}$ Pa using a commercial cryopump. After obtaining a desired vacuum, the valve between the cryopump and chamber was throttled and argon and oxygen gases were allowed to flow through the system at a pressure of 1.3 Pa. RF power was then applied to a commercial sputter gun with a 2.54 cm. diameter 99.999% Sn target.

Precautions can be taken to protect the devices from the effects of RF power. Such precautions include shielding the devices or gun using stainless steel screening, starting the gun with devices disconnected or grounded, avoiding the common use of a tesla coil or excessive RF power levels to ignite the plasma.

The microsubstrates were heated to deposition temperatures ranging from room temperature to 500° C. Bias control of microsubstrates to provide an additional lever of control on the deposition process was also found to be useful. Such bias can be applied to the heating element, the conductive heat distribution plate, or the contact pads. Moreover, each individual micro-hotplate in an array can be separately biased controlled for selective electroplating and bias sputtering deposition.

Deposition proceeded using 70 W RF power at a rate of 0–100 Å per second, and typically 10 Å per second. The rate was controlled by the RF power level. Deposition rate was monitored using an in situ quartz crystal monitor. Depending on the materials and deposition technique used, a much greater range of deposition rates may be used, e.g., up to 10000 Å per second. In some cases the deposition rate may depend on the micro-substrate temperature, for example, in a chemical vapor deposition process.

When the desired film thickness was reached, e.g., 0–10000 Å and typically 1000 Å the shutter to the deposition source was closed and the RF power was switched off. Individual microsubstrates were then cooled to room temperature over a time interval that ranged from 1 mS to 1 hour. Faster cooling rates may be obtained by increasing the thermal coupling of the microsubstrate to the rest of the chip, for example by shortening the microbridge supports. The cooling rate for each microsubstrate could be separately controlled by controlling current supplied to heating elements and monitoring the condition of the conductive heat distribution plate.

After the deposition process, the resulting samples can be subjected to various post processing treatments. These treatments included subsequent vacuum anneals, anneals in oxygen and hydrogen, argon ion sputtering, subsequent deposition of additional materials, and rapid thermal cycling.

Another deposition technique which can be used according to the present invention involves lithographically to define selected microsubstrates for deposition. For example, it is possible to coat an entire chip with a photoresist and thereafter expose selected micro-hotplates using a mask and appropriate illumination. Development proceeds by dissolving the exposed photoresist in a solvent in a known manner.

Subsequent deposition may proceed as described above or according to any known manner such as DC sputtering, thermal and electron beam evaporation, chemical vapor deposition, and the like.

After deposition, the remaining (non-exposed) photoresist coating may be lifted off using a solvent in a known manner. According to this procedure, deposition will only occur in the exposed areas. The sequence may be repeated to expose and deposit different materials on other microsubstrates.

Another lithographic technique which is unique to this microstructures of the present invention involves the use of the microheaters to create a maskless lithography process. This technique involves coating the entire microstructure with a resist material such as nitrocellulose or Shipley Resist 1470 or 1350J.

After coating with the resist, exposure is effected by simply heating the micro-hotplates upon which exposure is desired. In this unique method, the heat of the individual micro-hotplates causes the resist material to volatilize and burn off.

After the resist material is volatilized and burnt off selected micro-hotplates, deposition can then be performed as described above. After deposition, the remaining (non-volatilized) resist coating may be lifted off using a solvent, e.g., acetone in a known manner. This process provides a material film which is deposited only on the selectively heated micro-hotplates. The sequence may be repeated to expose and deposit different material films on other micro-hotplates.

Another lithographic technique which is unique to this microstructures of the present invention avoids the use of a resist material all together. According to this technique the entire microsubstrate is coated with a single material. This technique is useful for materials such as $SnO_2$ which are electrically conductive, when grown at a high temperature, or are electrically conductive when heated to a high temperature, but otherwise insulating when deposited on room temperature substrates.

According to this technique, individual micro-hotplates are heated during deposition or after deposition to become electrically conductive. The material deposited on unheated micro-hotplates and elsewhere on the chip was insulating, and therefore existed as a neutral layer which does not affect the performance of activated areas. This lithography technique defines electrically conductive areas by selectively activating the deposited film material.

According to the present invention films may be characterized in situ by their electrical conductance which can be measured by supplying current to two of the contact pads and measuring the voltage at the other two contact pads. This measurement can be done during deposition, or during or after various processing steps. During the course of the present invention, resistance changes from insulating to $1M\Omega$ were measured by heating a microsubstrate with an $SnO_2$ film in vacuum.

Multiple samples fabricated under different conditions may be examined using a variety of microcharacterization techniques, including scanning electron microscopy, energy dispersive x-ray analysis, optical microscopy, scanning tunneling microscopy, atomic force microscopy, etc. The micro samples, which comprise individual pixels on the final microsubstrate, can be studied in one session by mounting the microstructure in the desired instrumentation. Taking into account the time required for sample loading and the cost of operating such characterization instruments, characterization of samples using microsubstrate arrays is tremendously more efficient and economical than separate sample loadings that is required to study individual macroscopic samples. In addition, such instruments can be outfitted with sockets wired to outside instruments to provide facile in-situ characterization and processing capability.

Figure 6A:
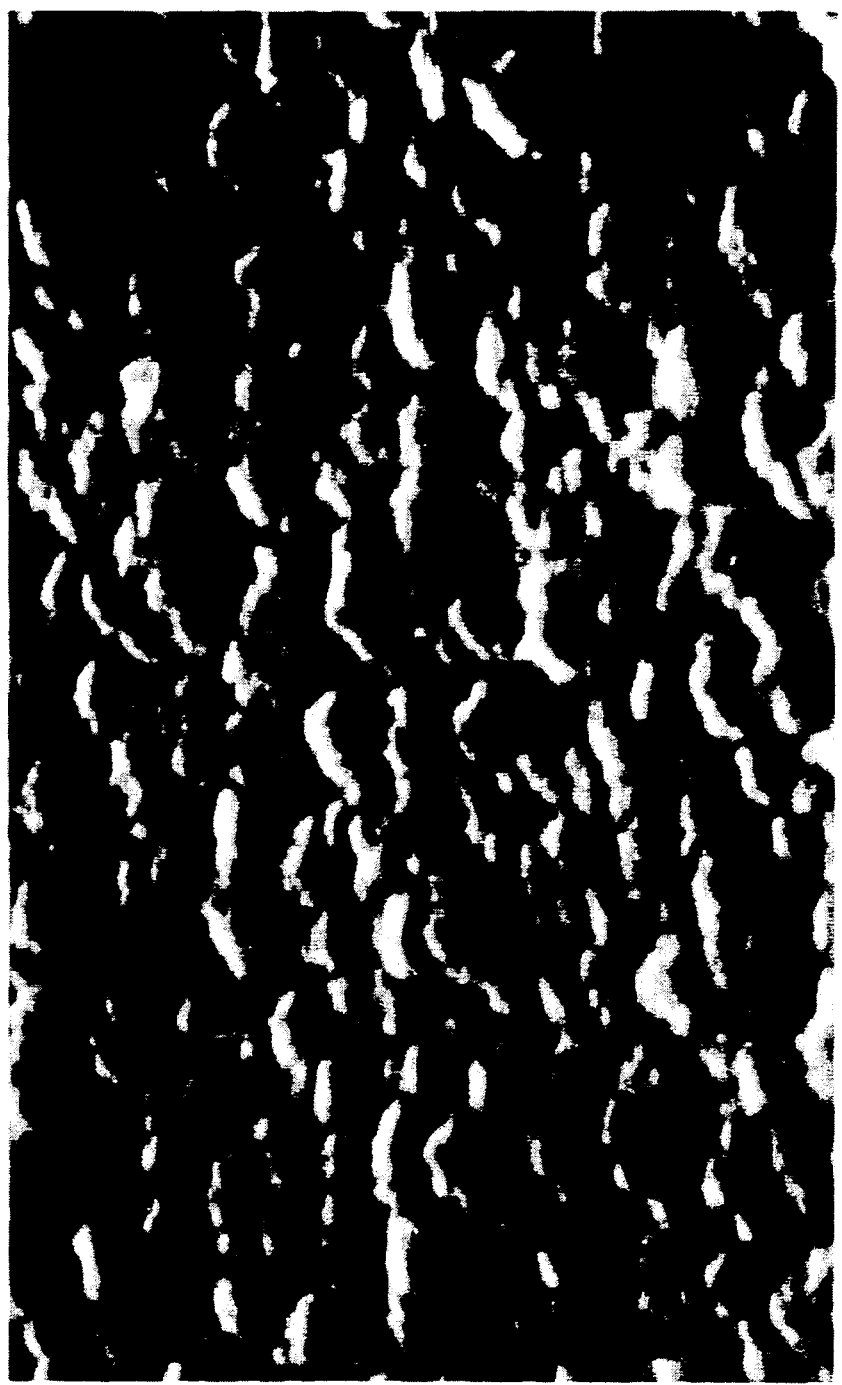
FIGS. 6A, 6B and 6C are scanning electron micrographs of $SnO_2$ grown on microsubstrates that were heated to room temperature (6A), 300° C. (6B) and 500° C. (6C), respectively during deposition.
Figure 6B:
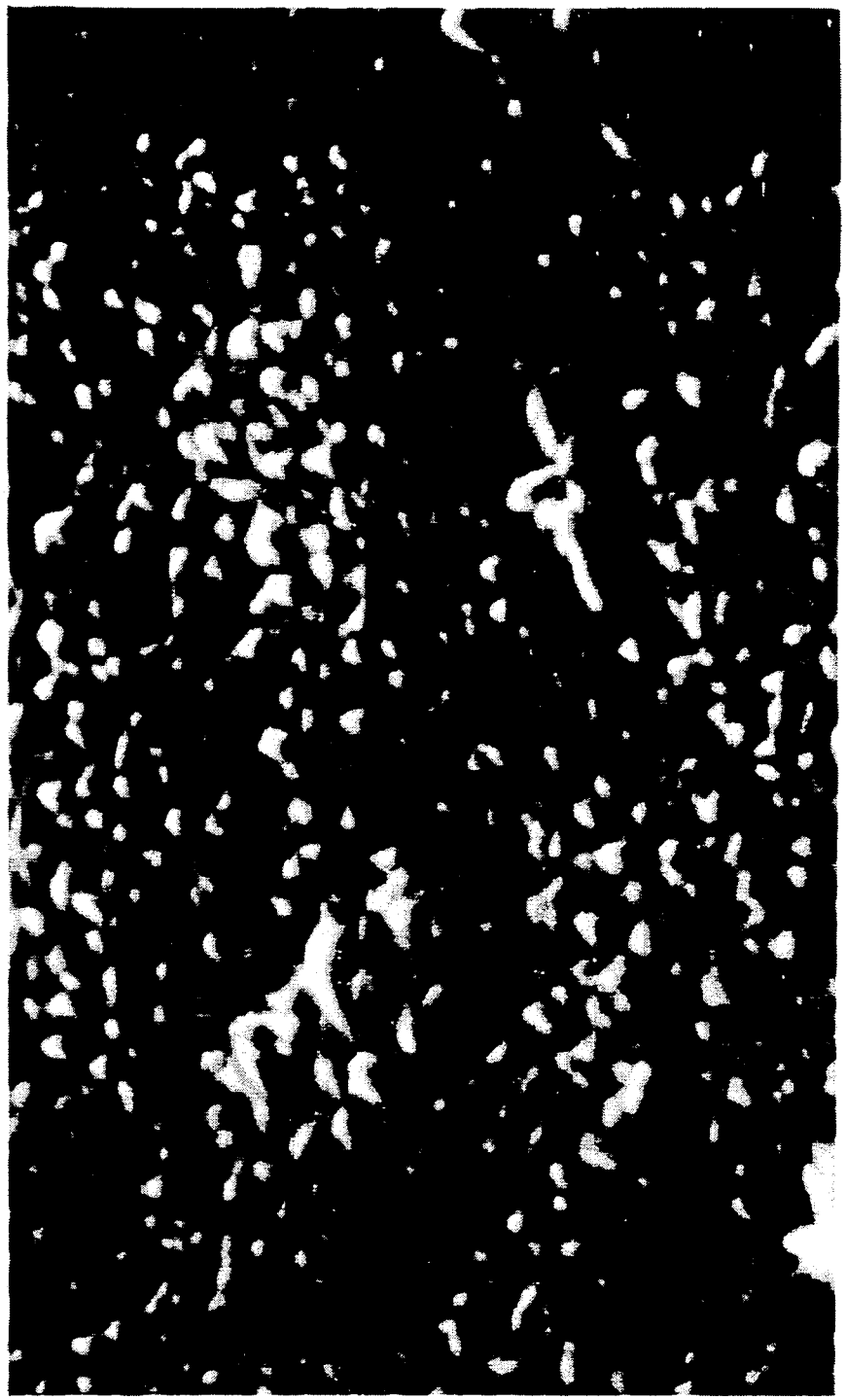
Figure 6C:

FIGS. 6A–6C are scanning electron micrographs of $SnO_2$ grown on microsubstrates that were heated to room temperature (6A), 300° C. (6B) and 500° C. (6C), respectively during deposition. Significant differences can be observed in the microstructures. These differences are associated with larger crystalline grain size at high temperatures, and an amorphous lumpy structure at room temperature.

The methods of the present invention combine the seemingly separate technologies of micromachining and film deposition, processing, lithography, and characterization to create a new technology for new device structures and materials development. An important feature of the invention is the use of commercial CMOS process to allow microsubstrates to be fabricated in quantity at low cost. According to the present invention, it has been shown herein that microsubstrates can be easily incorporated into existing deposition equipment.

Particular advantages of the present invention indicated above include the ability to thermally isolate individual substrate elements (micro-hotplates) from one another. This feature allows devices requiring high-temperature processing to occur on a microsubstrate without damaging other devices on the chip which may be more heat sensitive.

In addition, the methods of the present invention allow for each substrate element on the microsubstrate to receive a different sequence of temperatures during the deposition and post-process of a material. This allows a greatly enhanced development rate for materials process optimization, while reducing problems associated with recreating conditions reproducibly. The latter problem become more significant where repeated runs of macroscopic (>1 cm) samples are performed to optimize a process.

The methods used to create the microsubstrates used in the present invention are compatible with commercial CMOS ASIC foundries. Therefore, users do not need expensive equipment to produce microsubstrates. Moreover, since the methods are compatible, standard on-chip driver and multiplexer structures can be fabricated to address and control microsubstrate elements. This allows more microsubstrate elements to be controlled using fewer wires and also lowers the costs.

Because maskless lithography methods can be used as discussed above, the micro-hotplates themselves can be used to lithographically open deposition areas on addressed pixels thus eliminating the need of expensive photolithographic equipment.

The size and configuration of the micro-hotplates of the present invention allow for rapid temperature changes, low power consumption and low power radiation. The ability to undergo rapid temperature changes allows for thermal time constants of less than 1 mS thus enabling rapid quenching/annealing of microsubstrates to develop novel/non-equilibrium or amorphous materials. In addition, temperatures can be programmed to vary rapidly or slowly during a given process.

The power consumption of the micro-hotplates can be appreciated by the fact that they can be heated to 1200° C. with less than 100 mW of power required. As a comparison, heating a macroscopic (>1 cm) wafer to this temperature would typically require 100–1000 W.

Because of the small size, a microsubstrate heated to 1000° C. radiates little power. This allows high temperature processing of the sample to occur in delicate instruments such as scanning electron microscopes, scanning tunneling microscopes and atomic force microscopes, while proper function of the instrument would be impaired by heating a macroscopic sample to a comparable temperature.

The methods discussed herein are not limited to the field of materials processing only. Other areas of application are in electronic devices, materials science, solid state physics, and chemistry.

The methods presented herein can be directly applied to the fabrication of electronic devices where high temperature processing or device operation is required for some components on a chip, while other components cannot tolerate such high temperatures. For example the methods of the present invention are readily applicable to a chemical sensor which is based on a material whose properties are optimized by a high temperature process, such as a vacuum anneal. Semiconductor oxides are often used and have structural and compositional variation with processing at temperatures in excess of 400° C. Ohmic contacts to such a device can be achieved by heating the micro-hotplate so that there is some interdiffusion or alloying between the metal pads and the semiconducting oxide film. An alternate approach would be to provide crystalline Si on an exposed part of a thermally isolated substrate. In this approach epitaxial growth could occur on the Si. Optical semiconducting materials such as GaAs could then be grown on microheated Si substrates without thermally damaging other devices on the Si wafer.

As discussed above, the methods of the present invention are particularly useful for materials development process. For example the microstructure of a film coating can be optimized by adjusting film growth temperatures, and the rate at which the film is returned to room temperature after growth.

Processing of high temperature superconductor materials is another application in which the ability to heat a selected portion of the chip is advantageous. High temperature superconductor materials such as $YBa_2Cu_3O_{7-x}$ ($0 \leq X \leq 1$) require a high temperature post-growth heating in oxygen to produce superconducting properties. If such a high temperature treatment is applied to an entire chip, the performance of other devices on the wafer could adversely affected. By depositing the superconductor material on a heated pixel, and/or heating the superconducting material after the deposition thereof by selectively heating the pixel, heat affects on other areas of the microsubstrate can be avoided.

The superconductor can be used for many devices, including, for example, a superconducting bolometer. A bolometer is a device which measures longwave radiation via a temperature change. A superconductor maintained near the superconductor/normal transition, has a large resistance change for a small temperature change. A superconducting bolometer fabricated on the microsubstrates used in the present invention would have the advantages of being able to process the material(s) directly on isolated areas of the microsubstrate, the ability to selectively heat the superconductor material near its transition temperature, and the ability to produce a superconductor device of a low mass so that a small amount of radiation will produce a measurable temperature change.

Another example is in the area of materials reliability testing. Here, a film coating on a microsubstrate can be repeatedly cycled through a given temperature change until some failure of the coating were observed.

Another example is in electromigration studies. In this example, metal coatings of different compositions can be tested for electromigration effects by supplying a current through the film contact pads on the microsubstrate. These tests could be conducted at different temperatures, using the micro-hotplates.

Another example is to use the rapid short thermal time constant of the micro-hotplate to develop novel non-equilibrium phases of materials by rapid quenching and or heating. In another example parallel microsubstrates can be used as substrates for preparing and comparing biological samples.

In all of the above instances, the ability to simultaneously process hundreds of micro-samples with a range of temperature parameters would greatly enhance the optimization of the processes. Also the ability to examine many micro-samples in delicate micro-probing instruments (scanning electron microscope, scanning tunneling microscope, atomic force microscope, etc.) would speed the development process.

A commercial implementation may include a standard chip with 500 microsubstrates and associated drivers and multiplexers. Signals to the chip would address a micro-hotplate, set a heater current, measure a temperature, and measure a film conductance. A small microprocessor or personal computer would send these signals. Deposition and characterization equipment can be outfitted with sockets to accept the package into which this chip is mounted.

Solid state physics applications can take advantage of the small sample size, the rapid temperature change, and the low radiative power to study changes in solid state materials with temperature treatments. Melting transitions, and the physical changes which occur near these temperatures can be observed using micro-probing instruments (scanning electron microscope, scanning tunneling microscope, atomic force microscope, etc.).

The large thermal drifts associated with heating a large portion of the microscopes to study a macroscopic ($>1$ cm) sample can be avoided. These drifts often impair resolution. Stress-relaxation phenomena can be studied by applying short (of order 1 mS) pulses to the micro-hotplates and using real-time micro-probing instruments to observe relaxation phenomena. Novel non-equilibrium phases of materials, e.g., icosohedral quasicrystals, could be studied. Nanophase materials, such as small metal particles, can be deposited on a microsubstrate and observed with scanning tunneling microscopy. The diffusion and aggregation resulting from temperature treatments can be studied.

Chemical effects associated with a temperature processing of solid state film materials and their interaction with gaseous and plasma-activated gases can be studied. For example reactive ion etching of a material can be studied using the method of the present invention. In this regard, microsubstrates, coated with a film material of interest and heated to different temperatures, can be subjected to a reactive ion etch. Conductance of the film can be monitored, either in real time, or by interrupting the etch process. This would allow optimization of the temperature at which an etch process was carried out to obtain a desired etch rate. Films can be withdrawn from the etch process to examine structural-chemical changes using scanning electron microscopy and energy dispersive x-ray analysis.

In another example, chemical vapor deposition (CVD) processes can be studied. In this regard, micro-hotplates heated to different temperatures, can be subjected to a reactive CVD gas for a specified time. The sample can then be placed in a scanning electron microscope and a map of thickness vs. substrate temperature would be obtained.

In another example which involves the study of gas-surface interactions at different temperatures, micro-hotplates with a specific film coating can be heated to different temperatures, or subjected to different temperature cycling, and subjected to a gaseous environment of known pressure and composition. Conductance changes of the microfilms with gas exposure and temperature can provide a rapid picture of the nature of the chemical interactions occurring at the surface.

Although the present invention has been described with reference to particular means, materials and embodiments, from the foregoing description, one skilled in the art can easily ascertain the essential characteristics of the present invention and various changes and modifications may be made to adapt the various uses and characteristics without departing from the spirit and scope of the present invention as described by the claims which follow.

What is claimed is:

1. A method of preparing a plurality of micro-samples of materials for investigation which comprises:
   providing a substrate having a plurality of micro-hotplates, wherein each of said plurality of micro-hotplates can be individually temperature controlled; and
   depositing a material film on said plurality of micro-hotplates while thermally cycling selected ones of said plurality of micro-hotplates to form a micro-sample on each of said plurality of micro-hotplates.

2. A method of preparing a plurality of micro-samples of materials for investigation according to claim 1, wherein said step of thermally cycling selected ones of said micro-hotplates comprises heating all of said plurality of micro-hotplates to a common temperature.

3. A method of preparing a plurality of micro-samples of materials for investigation according to claim 1, wherein selected ones of said micro-samples are subjected to a post-deposition annealing treatment by heating selected ones of said micro-hotplates after said deposition step.

4. A method of preparing a plurality of micro-samples of materials for investigation according to claim 2, wherein selected ones of said micro-samples are subjected to a post-deposition annealing treatment by heating selected ones of said micro-hotplates after said deposition step.

5. A method of preparing a plurality of micro-samples of materials for investigation according to claim 1, further comprising performing a lithography process for isolating selected ones of said micro-hotplates prior to said deposition step.

6. A method of preparing a plurality of micro-samples of materials for investigation according to claim 5, wherein said lithography process involves applying a resist material to said substrate, irradiating portions of said resist material utilizing a mask and removing said irradiated portions of said resist material.

7. A method of preparing a plurality of micro-samples of materials for investigation according to claim 5, wherein said lithography process comprises a maskless-lithography process.

8. A method of preparing a plurality of micro-samples of materials for investigation according to claim 7, wherein said maskless-lithography process involves applying a resist material to said substrate and heating selected ones of said plurality of micro-hotplates to volatilize and thereby remove portions of said resist material.

9. A method of preparing a plurality of micro-samples of materials for investigation according to claim 1, wherein said step of depositing involves a sputtering process.

10. A method of preparing a plurality of micro-samples of materials for investigation according to claim 1, wherein said step of depositing involves a chemical vapor deposition process.

11. A method of preparing a plurality of micro-samples of materials for investigation according to claim 1, wherein said step of depositing involves an evaporation process.

12. A method of preparing a plurality of micro-samples of materials for investigation according to claim 1, wherein electrical properties of said material film are measured during said deposition.

13. A method of preparing a plurality of micro-samples of materials for investigation according to claim 3, wherein electrical properties of said material film are measured during said annealing.

14. A method of preparing a plurality of micro-samples of materials for investigation according to claim 4, wherein electrical properties of said material film are measured during said annealing.

15. A method of characterizing material properties which comprises:
   providing a substrate having a plurality of micro-hotplates, wherein each of said plurality of micro-hotplates can be individually temperature controlled;
   depositing a material film on said plurality of micro-hotplates while thermally cycling selected ones of said plurality of micro-hotplates to form a micro-sample on each of said plurality of micro-hotplates; and
   characterizing properties of said micro-samples.

16. A method of characterizing material properties according to claim 15, wherein said properties of said micro-samples which are characterized are selected from the group consisting of electrical properties, chemical properties, physical properties and combinations thereof.

17. A method of characterizing material properties according to claim 15, wherein said characterization is performed during said deposition step.

18. A method of characterizing material properties according to claim 15, wherein said characterization is performed by scanning electron microscopy, scanning tunneling microscopy, atomic force microscopy or x-ray analysis.

19. A method of characterizing material properties according to claim 15, wherein selected ones of said micro-samples are subjected to a post-deposition annealing treatment by heating selected ones of said micro-hotplates after said deposition step.

20. A method of characterizing material properties according to claim 15, wherein said step of thermally cycling selected ones of said micro-hotplates comprises heating all of said plurality of micro-hotplates to a common temperature.

* * * * *